(12) United States Patent
Shanmugam et al.

(10) Patent No.: US 8,630,448 B1
(45) Date of Patent: Jan. 14, 2014

(54) METHOD AND SYSTEM FOR IMAGE-BASED NUTRITION/HEALTH MONITORING

(75) Inventors: Elangovan Shanmugam, Cupertino, CA (US); Muhammet Serdar Akin, Santa Clara, CA (US); Andries Schutte, Raleigh, NC (US)

(73) Assignee: Intuit Inc., Mountain View, CA (US)

( * ) Notice: Subject to any disclaimer, the term of this patent is extended or adjusted under 35 U.S.C. 154(b) by 109 days.

(21) Appl. No.: 13/274,120

(22) Filed: Oct. 14, 2011

(51) Int. Cl.
*G06K 9/00* (2006.01)
*G09B 19/00* (2006.01)

(52) U.S. Cl.
USPC .......................................... 382/100; 434/127

(58) Field of Classification Search
USPC ................. 382/100, 110, 165, 181; 600/300;
426/11, 61, 71, 86, 119, 389, 499;
705/2; 434/127; 128/921, 920, 922
See application file for complete search history.

(56) References Cited

U.S. PATENT DOCUMENTS

| 5,454,721 | A | * | 10/1995 | Kuch | 434/127 |
| 6,585,516 | B1 | * | 7/2003 | Alabaster | 434/127 |
| 2005/0113649 | A1 | * | 5/2005 | Bergantino | 600/300 |
| 2012/0005222 | A1 | * | 1/2012 | Bhagwan et al. | 707/769 |

* cited by examiner

*Primary Examiner* — Abolfazl Tabatabai
(74) *Attorney, Agent, or Firm* — McKay and Hodgson, LLP; Philip McKay; Sean P. Lewis

(57) ABSTRACT

Data indicating a user's desired, and/or mandated/prescribed, dietary guidelines and/or restrictions is obtained from one or more sources and then when the user is frequenting a restaurant, fast food establishment, supermarket, or any other establishment for obtaining food, an optical image of printed or visual nutritional information associated with the food item the user is contemplating purchasing/eating is obtained via one or more user computing systems. Optical Character Recognition (OCR) technology is then used to transform the printed/visual nutritional information contained in the optical image into discrete nutritional information data. The nutritional information data is then analyzed and compared with the data indicating the user's desired, and/or mandated/prescribed, dietary guidelines and/or restrictions and a recommendation is made to the user as to whether the contemplated food item is a good/acceptable purchase for the user, and/or whether the user should eat/purchase the food item.

29 Claims, 2 Drawing Sheets

METHOD AND SYSTEM FOR IMAGE-BASED NUTRITION/HEALTH MONITORING

BACKGROUND

Today, more than ever, people are interested in monitoring and tracking their food intake and, in particular, trying to ensure that their dietary habits are in line with various general health recommendations. In addition, millions of people have one or more conditions, illnesses, or diseases, which require them to closely scrutinize and monitor all food they consume and minimize their intake of certain elements and types of food.

However, one of the more difficult challenges facing anyone trying to monitor and control their food and nutrient intake is the challenge of a trying to eat in a healthy, and/or prescribed, manner when eating outside the home, i.e., when dining/eating out. Given that many people are regularly forced to eat outside the home due to time constraints, travel, convenience, and social needs, the challenge of trying to eat "right" while dining out is very real and often encountered on an almost daily basis.

Recently, restaurants, fast food establishments, and other providers of food items, have begun printing the nutritional information associated with their menu, or other food offerings, on the menu, or food product itself, and/or on handouts or displays provided at the food offering facilities. However, for the average person, deciphering and then keeping track of this printed/visual nutritional information is often extremely time-consuming and difficult. This is particularly true when, as noted above, many people utilize restaurants and fast food establishments on a frequent basis so that a running or cumulative tracking of the printed/visual nutritional information, often from multiple establishments/sources, is required in order to obtain a realistic indication of how healthy the person is actually eating.

The situation is problematic enough for relatively "healthy people" who can often choose to ignore their food intake on occasion, or even for extended periods of time. However, for millions of people having various health conditions, such as diabetes, high blood pressure, allergies, heart disease, etc., ignoring their food intake, even occasionally, is not an option and, in some cases, can be quite dangerous.

Despite the desire, and in many cases the very real need, for people to relatively closely monitor their food intake, and even though many establishments/food providers do provide printed/visual nutritional information for their food offerings, there is currently no simple and efficient way for a consumer to accurately, and in relative real time, obtain data indicating the nutritional information associated with food offerings and then determine, based on the nutritional information, if the food offerings are in line with the consumers desired, and/or mandated/prescribed, nutritional requirements and/or limitations.

What is needed is a method and system that allows users to capture printed and/or visual nutritional information associated with food offerings/items and then automatically compare that nutritional information with the nutritional and/or dietary requirements and/or limitations of the particular user.

SUMMARY

In accordance with one embodiment, a method and system for image based nutrition monitoring includes a process for image based nutrition monitoring whereby, in one embodiment, data indicating a user's desired, and/or mandated/prescribed, dietary guidelines and/or restrictions is obtained from one or more sources. In one embodiment, when the user is frequenting a restaurant, fast food establishment, supermarket, or any other establishment for obtaining food, an optical image of printed or visual nutritional information associated with the food item the user is contemplating purchasing/eating is obtained via one or more user computing systems. In one embodiment, Optical Character Recognition (OCR) technology is used to transform the printed/visual nutritional information contained in the optical image into discrete nutritional information data. The nutritional information data is then analyzed and compared with the data indicating the user's desired, and/or mandated/prescribed, dietary guidelines and/or restrictions. In one embodiment, based, at least in part, on this analysis and comparison, and, in one embodiment, on data indicating the users recent nutritional/food intake, a recommendation is made to the user as to whether the contemplated food item is a good/acceptable purchase for the user, and/or whether the user should eat/purchase the food item. In one embodiment, the user is additionally provided with advice regarding limitations on future food purchases, and/or intake, which should be considered if the contemplated food item is indeed consumed.

In one embodiment, the method and system for image based nutrition monitoring discussed herein utilizes readily and commonly available image capture technology, such as a camera function on a mobile phone, and Optical Character Recognition (OCR) technology, to capture printed nutritional information regarding contemplated food purchases and transform the printed nutritional information into usable nutritional information data that can be analyzed by one or more processors associated with one or more computing systems. The nutritional information data so obtained is then processed and compared with data representing the individual nutritional desires/needs of the user by one or more processors so that the user can easily, efficiently, and semi-automatically, track their nutritional intake and obtain dietary advice that is consistent with the users specific nutritional and/or dietary requirements, and/or dietary limitations.

As a result, the method and system for image based nutrition monitoring discussed herein provides users the ability to easily and efficiently maintain healthy eating habits in virtually all circumstances, including in situations when the user dines out and/or is in the store contemplating a food purchase.

As discussed in more detail below, using the below embodiments, with little or no modification, there is considerable flexibility, adaptability, and opportunity for customization to meet the specific needs of various healthcare consumers under numerous circumstances.

BRIEF DESCRIPTION OF THE DRAWINGS

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims below.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

In one embodiment, the process for image based nutrition monitoring is implemented, at least in part, and/or associated with, one or more user computing systems that include a camera, or other optical image capturing capability.

Herein the term "computing system" includes, but is not limited to, any computing system known in the art at the time of filing, and/or as developed after the time of filing, such as, but not limited to: a mobile computing system; a desktop computing system; a laptop computing system; a notebook computing system; a workstation; a two-way pager; a cellular telephone; a smart phone; a digital wireless telephone; a Personal Digital Assistant (PDA); a server computer; an Internet appliance, and/or any other device, or any desired combination of these devices, that includes components that can execute all, or part, of a process for image based nutrition monitoring in accordance with at least one of the embodiments as discussed herein, and/or as known in the art at the time of filing, and/or as developed after the time of filing.

In one embodiment, the user computing system including a camera and/or optical image capture capability is a mobile computing system. Herein, the term "mobile computing system" includes, but not limited to: a mobile phone; a smart phone; an internet appliance; any SMS capable system; or any other mobile computing system as discussed herein, and/or as known in the art at the time of filing, and/or as developed after the time of filing.

In accordance with one embodiment, a method and system for image based nutrition monitoring includes a process for image based nutrition monitoring whereby, in one embodiment, data indicating a user's desired, and/or mandated/prescribed, dietary guidelines and/or restrictions is obtained from one or more sources.

In various embodiments, the user's desired, and/or mandated/prescribed, dietary guidelines/restrictions data is obtained from one or more sources including, but not limited to, the user's medical records data as maintained by the user.

In various embodiments, the user's desired, and/or mandated/prescribed, dietary guidelines/restrictions data is obtained from one or more sources including, but not limited to, the user's medical records data as maintained by, and/or associated with, one or more healthcare service providers associated with the user, such as the user's primary care physician.

In various embodiments, the user's desired, and/or mandated/prescribed, dietary guidelines/restrictions data is obtained from one or more sources including, but not limited to, one or more computing systems, data management systems, databases, and/or websites maintained by, and/or associated with, one or more data management systems, such as the QuickenHealth™ series of systems available from Intuit, Inc. of Mountain View, Calif.

In various embodiments, the user's desired, and/or mandated/prescribed, dietary guidelines/restrictions data is obtained from one or more sources including, but not limited to, one or more computing systems, data management systems, databases, and/or websites maintained by, and/or associated with, one or more healthcare insurance providers associated with the user.

In various embodiments, the user's desired, and/or mandated/prescribed, dietary guidelines/restrictions data is obtained from one or more sources including, but not limited to, one or more computing systems, data management systems, databases, and/or websites maintained by, and/or associated with, one or more health related agencies such as, but not limited to, the Food and Drug Administration (FDA), the American Heart Association (AHA), the American Cancer Society (ACS), the Mayo Clinic, etc.

In various embodiments, the user's desired, and/or mandated/prescribed, dietary guidelines/restrictions data is obtained from one or more sources including, but not limited to, one or more computing systems, data management systems, databases, and/or websites maintained by, and/or associated with, one or more diet providers and/or diet plan developers/promoters.

In various embodiments, the user's desired, and/or mandated/prescribed, dietary guidelines/restrictions data is obtained from one or more sources including, but not limited to, manual input provided by the user through a user computing system and one or more user interface devices such as, but not limited to, a keyboard, mouse, touch bad, touchscreen, voice recognition system, or any other device or mechanism for transforming one or more user actions into computer executable instructions and/or actions.

In various embodiments, the user's desired, and/or mandated/prescribed, dietary guidelines/restrictions data is obtained from any source of dietary guidelines/restrictions data as discussed herein, and/or as known/available in the art at the time of filing, and/or as known/developed after the time of filing.

In various embodiments, the user's desired, and/or mandated/prescribed, dietary guidelines/restrictions data is then stored/saved in a database or any computing system, as discussed herein, and/or as known in the art/available at the time of filing, and/or as developed/made available after the time of filing.

Herein, the term "database" can refer to a dedicated mass storage device implemented in software, hardware, or a combination of hardware and software. Herein, the term "database" can refer to a web-based function. Herein, the term "database" can refer to any data storage means that is part of, or under the control of, any computing system, as defined herein, known at the time of filing, or as developed thereafter.

For instance, in one embodiment, the user's desired, and/or mandated/prescribed, dietary guidelines/restrictions data is saved/stored in whole, or in part, in a memory system, or in a cache memory, or in any main memory or mass memory, associated with any computing system as discussed herein, and/or as known/available in the art at the time of filing, and/or as developed/made available after the time of filing. In one embodiment, the user's desired, and/or mandated/prescribed, dietary guidelines/restrictions data in whole, or in part, is stored in any computing system and/or server system, or other device, in another location, or on/in a computer readable medium, and/or any other computer program product, as defined herein. In one embodiment, the user's desired, and/or mandated/prescribed, dietary guidelines/restrictions data in whole, or in part, is stored on a webpage, in a web-based system, or on a public network such as the Internet.

In some embodiments, the user's desired, and/or mandated/prescribed, dietary guidelines/restrictions data, stored as described above, is maintained, in whole, or in part, by: the process for image based nutrition monitoring, and/or a provider of the process for image based nutrition monitoring; a data management system, and/or a provider of a data management system; a third party data storage institution; any third party service or institution; and/or any other parties. In some of these embodiments, access to the data is then provided to the process for image based nutrition monitoring by providing access to the data and/or providing the data on a computer program product.

As noted above, recently restaurants, fast food establishments, supermarkets, and providers of food items have begun providing nutritional information regarding their food related offerings in printed formats, such as on menus, labels, flyers, and visual displays.

In one embodiment, when the user is frequenting a restaurant, fast food establishment, supermarket, or any other establishment for obtaining food, the user uses a user computing system, and camera or other optical image capturing capability, to obtain an optical image of the printed or visual nutritional information associated with a food item the user is contemplating purchasing/eating.

In one embodiment, the captured optical image of the printed or visual nutritional information is processed using Optical Character Recognition (OCR) technology under the control of one or more processors associated with one or more computing systems. In one embodiment, the OCR technology is used by one or more processors to transform the printed/visual nutritional information contained in the optical image into discrete nutritional information data.

In one embodiment, the nutritional information data is then analyzed and compared with the data indicating the user's desired, and/or mandated/prescribed, dietary guidelines and/or restrictions using one or more processors associated with one or more computing systems.

As a specific illustrative example, in one embodiment the nutritional information data is analyzed using one or more processors associated with one or more computing systems to determine the sugar content, and/or carbohydrate content, of a given food item and then this data is compared with sugar and/or carbohydrate intake guidelines provided by a user's physician using one or more processors associated with one or more computing systems.

In one embodiment, the nutritional information data associated with the food item currently being considered is combined with nutritional information data associated with food items recently purchased and or consumed by the user using one or more processors associated with one or more computing systems, and then the combined data is analyzed and compared with the data indicating the user's desired, and/or mandated prescribed, dietary guidelines and/or restrictions using one or more processors associated with one or more computing systems.

As another specific illustrative example, in one embodiment the nutritional information data for a menu item, such as a specific dinner selection, is analyzed using one or more processors associated with one or more computing systems to determine the calories of the specific dinner selection. Then this data is combined with nutritional information, and in particular the caloric information, associated with the other food selections made and entered into process for image based nutrition monitoring by the user within the last 24 hours. Then the combined caloric intake for the past 24 hours is compared with FDA guidelines for the number of calories that should be consumed by a person similar to the user using one or more processors associated with one or more computing systems.

In one embodiment, based, at least in part, on the analysis and comparison of the data indicating the user's desired, and/or mandated/prescribed, dietary guidelines and/or restrictions and the nutritional information data associated with the food item currently under consideration, and, in one embodiment, data associated with food items recently consumed, a recommendation is made to the user as to whether the contemplated food item is a good/acceptable purchase for the user, and/or whether the user should eat/purchase the food item.

In one embodiment, the recommendation as to whether the contemplated food item is a good/acceptable purchase for the user, and/or whether the user should eat/purchase the food item, is provided to the user via the user computing system and/or one or more other computing systems accessible by the user.

In one embodiment, the nutritional information data associated with the user is saved/stored for at least a defined time frame and the user is additionally provided with advice regarding limitations on future food purchases, and/or intake, which should be considered if the contemplated food item is indeed consumed.

For instance, as one specific illustrative example, if the user decides to consume a food item whose nutritional information data indicated 2000 calories, and the FDA recommendation for total caloric intake for the user is 2500 calories per day, in one embodiment, the process for image based nutrition monitoring would inform the user that the user can only consume 500 more calories that day and recommend the user consider eating lightly the remainder of the day.

Hardware System Architecture

Figure 1:
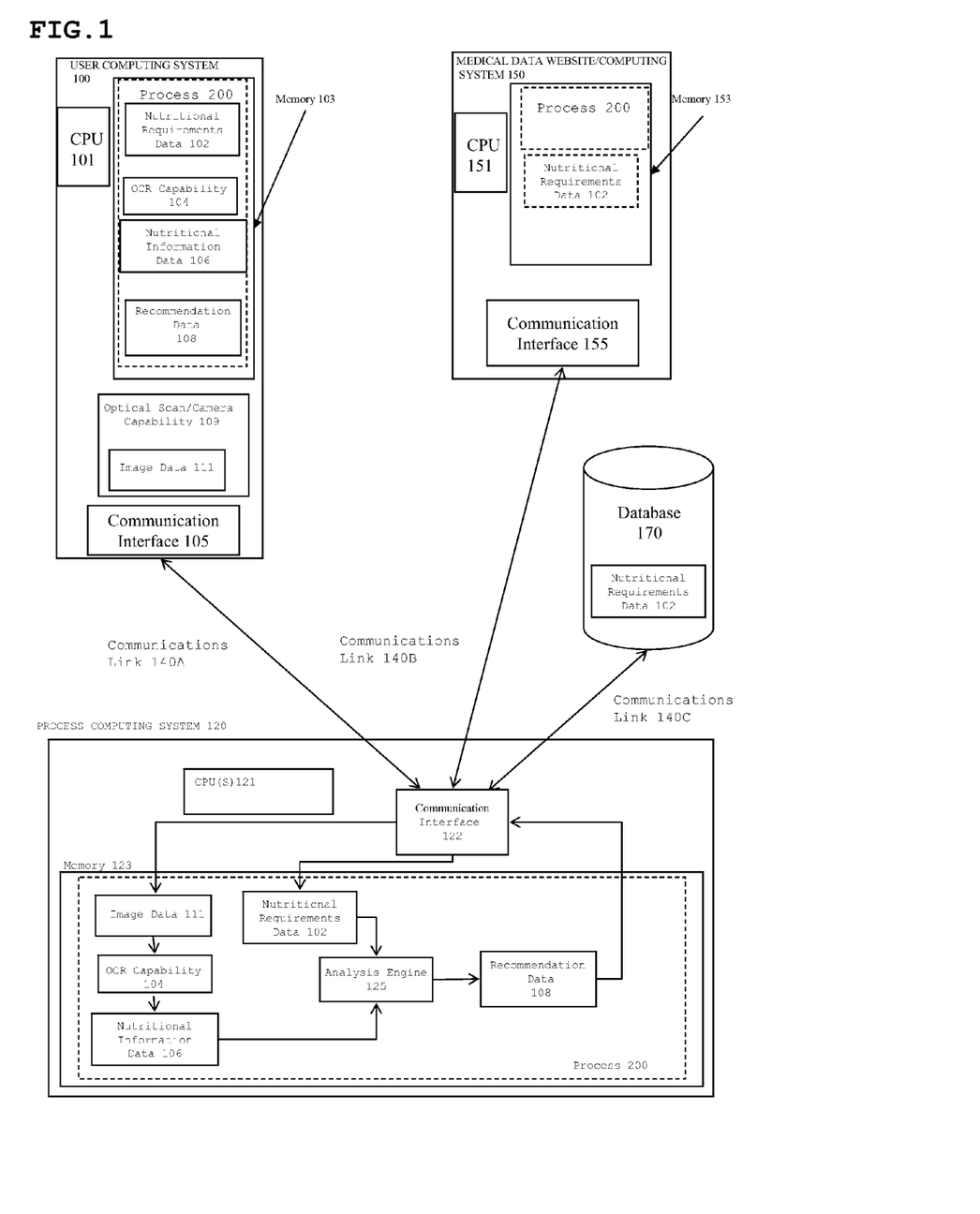
FIG. 1 is a block diagram of an exemplary hardware architecture for implementing one embodiment.

FIG. 1 is a block diagram of an exemplary hardware architecture for implementing one embodiment of a method and system for image based nutrition monitoring, such as exemplary process 200 discussed herein, that includes: a user computing system 100, e.g., a first computing system; a medical data website/computing system 150, e.g., a second computing system; a process computing system 120, e.g., a third computing system or server system; a database 170; a communications link 140A, e.g., a first communications link; a communications link 140B, e.g., a second communications link; and communications link 140C, e.g., a third communications link.

As seen in FIG. 1, user computing system 100 typically includes a central processing unit (CPU) 101, a communications interface 105, a memory system 103, and an optical scan/camera capability 109, including image data 111.

In one embodiment, user computing system includes optical scan/camera capability 109, including image data 111. As noted above, recently restaurants, fast food establishments, supermarkets, and providers of food items have begun providing nutritional information regarding their food related offerings in printed formats, such as on menus, labels, flyers, and visual displays.

In one embodiment, when the user is frequenting a restaurant, fast food establishment, supermarket, or any other establishment for obtaining food, the user uses user computing system 100, and optical scan/camera capability 109, to obtain image data 111 of the printed or visual nutritional information associated with a food item the user is contemplating purchasing/eating.

In one embodiment, memory system 103 includes all, or part of, a process for image based nutrition monitoring 200, shown as process 200 in FIG. 1.

In one embodiment, memory system 103 includes all, or part of, nutritional requirements data 102 that includes data, processes, and/or procedures for obtaining and storing a user's desired, and/or mandated/prescribed, dietary guidelines and/or restrictions from any one or more sources as discussed herein.

In one embodiment, memory system 103 includes all, or part of, OCR capability 104 including data, processes and/or procedures for transforming the nutritional information contained in image data 111 into discrete nutritional information data 106.

As noted above, in one embodiment, the captured image data 111 of the printed or visual nutritional information is processed using OCR capability 104 under the control of one or more processors associated with one or more computing systems, such as CPUs 101 and/or 121 of FIG. 1, to transform the printed/visual nutritional information contained in image data 111 into nutritional information data 106.

Returning to FIG. 2, in one embodiment, nutritional information data 106 is then analyzed and compared with nutritional requirements data 102 using one or more processors associated with one or more computing systems such as CPUs 101 and/or 121 of FIG. 1, to generate recommendation data 108 that includes a recommendation to the user as to whether the contemplated food item is a good/acceptable purchase for the user, and/or whether the user should eat/purchase the food item.

Returning to FIG. 2, in one embodiment, user computing system 100 is any computing system discussed herein, and/or as known in the art at the time of filing, and/or as developed after the time of filing that includes components that can execute all, or part, of process for image based nutrition monitoring 200 in accordance with at least one of the embodiments as described herein.

Herein the term "computing system" includes, but is not limited to, any computing system known in the art at the time of filing, and/or as developed after the time of filing, such as, but not limited to: a mobile computing system; a desktop computing system; a laptop computing system; a notebook computing system; a workstation; a two-way pager; a cellular telephone; a smart phone; a digital wireless telephone; a Personal Digital Assistant (PDA); a server computer; an Internet appliance, and/or any other device, or any desired combination of these devices, that includes components that can execute all, or part, of a process for image based nutrition monitoring in accordance with at least one of the embodiments as discussed herein, and/or as known in the art at the time of filing, and/or as developed after the time of filing.

In one embodiment, user computing system 100 is a mobile computing system. Herein, the term "mobile computing system" includes, but not limited to: a mobile phone; a smart phone; an internet appliance; any SMS capable system; or any other mobile computing system as discussed herein, and/or as known in the art at the time of filing, and/or as developed after the time of filing.

In various embodiments, user computing system 100 may further include standard user interface devices such as a keyboard (not shown), a mouse (not shown), a printer (not shown), and a display device (not shown), as well as, one or more standard input/output (I/O) devices (not shown), such as a compact disk (CD) or Digital Video Disc (DVD) drive, floppy disk drive, or other device capable of inputting data to, and outputting data from, user computing system 100, whether available or known at the time of filing or as later developed.

In one embodiment, process for image based nutrition monitoring 200 is entered, in whole, or in part, into user computing system 100 via an I/O device (not shown), such as from a CD, DVD, floppy disk, portable hard drive, memory stick, download site, or other medium and/or computer program product as defined herein.

As also seen in FIG. 1, medical data website/computing system 150 typically includes a central processing unit (CPU) 151, a communications interface 155, and a memory system 153. In one embodiment, memory system 153 includes all, or part of, process for image based nutrition monitoring 200, shown as process 200 in FIG. 1.

In one embodiment, memory system 153 includes all, or part of, nutritional requirements data 102.

In various embodiments medical data website/computing system 150 is associated with one or more healthcare service providers associated with the user, such as the user's primary care physician.

In various embodiments medical data website/computing system 150 is maintained by, and/or associated with, one or more data management systems, such as the Quicken-Health™ series of systems available from Intuit, Inc. of Mountain View, Calif.

In various embodiments medical data website/computing system 150 is maintained by, and/or associated with, one or more healthcare insurance providers associated with the user.

In various embodiments medical data website/computing system 150 is maintained by, and/or associated with, one or more health related agencies such as, but not limited to, the Food and Drug Administration (FDA), the American Heart Association (AHA), the American Cancer Society (ACS), the Mayo Clinic, etc.

In various embodiments medical data website/computing system 150 is maintained by, and/or associated with, one or more diet providers and/or diet plan developers/promoters.

In one embodiment, medical data website/computing system 150 is any computing system discussed herein, and/or as known in the art at the time of filing, and/or as developed after the time of filing that includes components that can execute all, or part, of process for image based nutrition monitoring 200 in accordance with at least one of the embodiments as described herein.

In various embodiments, medical data website/computing system 150 may further include standard user interface devices such as a keyboard (not shown), a mouse (not shown), a printer (not shown), and a display device (not shown), as well as, one or more standard input/output (I/O) devices (not shown), such as a compact disk (CD) or Digital Video Disc (DVD) drive, floppy disk drive, or other device capable of inputting data to, and outputting data from, user computing system 100, whether available or known at the time of filing or as later developed.

As seen in FIG. 1, in one embodiment, process computing system 120 includes one or more processors, CPU(s) 121, a communication interface 122, and a memory 123.

As seen in FIG. 1, in one embodiment, memory 123 includes all, or part of, process for image based nutrition monitoring 200, shown as process 200 in FIG. 1.

In one embodiment, memory system 153 includes all, or part of, nutritional requirements data 102 from user computing system 100 and/or medical data website/computing system 150, that includes data, processes, and/or procedures for obtaining and storing a user's desired, and/or mandated/prescribed, dietary guidelines and/or restrictions from any one or more sources as discussed herein.

In one embodiment, memory system 153 includes all, or part of, OCR capability 104 including data, processes and/or procedures for transforming the nutritional information contained in image data 111 from optical scan/camera capability 109 of user computing system 100 into discrete nutritional information data 106.

As noted above, in one embodiment, the captured image data 111 of the printed or visual nutritional information is processed using OCR capability 104 under the control of one or more processors associated with one or more computing systems, such as CPUs 121 and/or 101 of FIG. 1, to transform the printed/visual nutritional information contained in image data 111 into nutritional information data 106.

Returning to FIG. 2, in one embodiment, nutritional information data 106 is then analyzed and compared with nutritional requirements data 102 using one or more processors associated with one or more computing systems, such as CPUs 121 and/or 101 of FIG. 1, and analysis engine 125, to generate recommendation data 108 that includes a recommendation to the user as to whether the contemplated food item is a good/acceptable purchase for the user, and/or whether the user should eat/purchase the food item.

Returning to FIG. 2, in one embodiment, recommendation data 108 is then sent from process computing system 120 to user computing system 100 using communications link 140A.

In various embodiments, process computing system 120 is any computing system discussed herein, and/or as known in the art at the time of filing, and/or as developed after the time of filing that includes components that can execute all, or part, of a process for image based nutrition monitoring, in accordance with at least one of the embodiments as described herein.

Also shown in FIG. 1 is database 170. In one embodiment, database 170 is a data storage device, a designated server system or computing system, or a designated portion of one or more server systems or computing systems, such as computing systems 100, 150 and 120, or a distributed database, or an external and/or portable hard drive. In one embodiment, database 170 is a dedicated mass storage device implemented in software, hardware, or a combination of hardware and software. In one embodiment, database 170 is a web-based function.

As discussed in more detail below, in one embodiment, database 170 is under the control of a process for image based nutrition monitoring, such as exemplary process 200, and includes all, or part of, nutritional requirements data 102, OCR capability 104, balance display symbols data 106, current balance data 108, and/or designated applications 107.

In various embodiments, database 170 is associated with one or more healthcare service providers associated with the user, such as the user's primary care physician, and includes nutritional requirements data 102.

In various embodiments, database 170 is maintained by, and/or associated with, one or more data management systems, such as the QuickenHealth™ series of systems available from Intuit, Inc. of Mountain View, Calif.

In various embodiments, database 170 is maintained by, and/or associated with, one or more healthcare insurance providers associated with the user.

In various embodiments, database 170 is maintained by, and/or associated with, one or more health related agencies such as, but not limited to, the Food and Drug Administration (FDA), the American Heart Association (AHA), the American Cancer Society (ACS), the Mayo Clinic, etc.

In various embodiments, database 170 is maintained by, and/or associated with, one or more diet providers and/or diet plan developers/promoters.

In one embodiment, computing systems 100 and 150, and database 170, are linked to process computing system 120 via communications channels 140A, 140B, and 140C, respectively. In various embodiments, any, or all, of communications channels 140A, 140B, and 140C can be, but are not limited to: a mobile communication link, such as a mobile phone link; a land-line phone link; a cable-based communications link; a satellite communications link; the Internet, or other network communications link; and/or any other communications link, or combination of communications links, as discussed herein, and/or as known in the art at the time of filing, and/or as developed after the time of filing.

In various embodiments, any, or all, of communications channels 140A, 140B, and 140C, are any SMS communication link as discussed herein, and/or as known in the art at the time of filing, and/or as developed after the time of filing. Short Message Service (SMS) is the text communication service component of phone, web, or mobile communication systems. SMS uses relatively ridged standardized communications protocols that allow the exchange of only very short text messages between fixed line or mobile phone devices in "SMS format".

In various embodiments any, or all, of communications channels 140A, 140B, and 140C include any network or network system that is of interest to a consumer such as, a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

In one embodiment, computing systems 100 and 150, database 170, process computing system 120, and any, or all, of communications channels 140A, 140B, and 140C, are part of a cloud computing environment.

Those of skill in the art will readily recognize that the components shown in FIG. 1 and their respective sub-components, are shown for illustrative purposes only and that architectures with more or fewer components can implement, and benefit from, the invention. Moreover, one or more components may be located remotely from their respective system and accessed via network, as discussed herein. In addition, the particular type of, and configuration of, computing systems 100, 150, database 170, and process computing system 120 are not relevant.

Although a process for image based nutrition monitoring, such as process for image based nutrition monitoring 200, is sometimes referred to herein, alternatively, as a process, an application, a module, a program, a component of a software system, a component of a software package, a component of a parent system, a plug-in, or a feature of a parent system, this terminology is illustrative only. In some embodiments, a process for image based nutrition monitoring, such as process for image based nutrition monitoring 200, is capable of being called from an application or the operating system. In one embodiment, an application, process, or program is generally defined to be any executable code. Moreover, those of skill in the art will understand that when it is said that an application, process, or an operation takes some action, the action is the result of executing one or more instructions by a processor, such as CPU(s) 101, 151, and/or 121.

In one embodiment, a process for image based nutrition monitoring, such as process for image based nutrition monitoring 200, is a computer application or process implemented and/or run and/or stored, in full, or in part, in, or on, a computer program product. Herein, a computer program product comprises a medium and/or I/O device configured to store or transport computer readable code, whether available or known at the time of filing or as later developed. Some examples of computer program products are CDs, DVDs, ROM cards, floppy discs, magnetic tapes, computer hard drives, portable hard drives, flash memory, volatile and non-volatile memory sticks, servers on a network, or other media or process capable of delivering computer readable data representing computer readable code, whether available or known at the time of filing or as later developed. This medium may belong to a computing system, such as computing systems 100, 120, and 150 of FIG. 1, described above. However, in some embodiments, the medium also may be removable and/or remote from the computing system.

Process

Herein, the terms "user", "healthcare consumer", "consumer", are used interchangeably to denote any person, party, or parties, who provide their information to, or for whom information is gathered by, a process for image based nutrition monitoring, or for whom interaction with a process for image based nutrition monitoring is performed, and/or an authorized agent of any person, party, or parties, who provide their information to, or for whom information is gathered by, a process for image based nutrition monitoring, or for whom interaction with a process for image based nutrition monitoring is performed.

Herein, the term "healthcare provider" and/or "healthcare service provider" denotes any individual person, persons, agencies, institutions, organizations, businesses, and/or other entities that provide medical healthcare regimen, medications, therapy, advice, and/or equipment. For example, herein, the term "healthcare provider" includes, but is not limited to: doctors; nurses; technicians; therapists; pharmacists; laboratories; counselors; alternative medicine practitioners; medical facilities; doctor's offices; hospitals; emergency rooms; clinics; urgent care centers; alternative medicine clinics/facilities; physical therapy clinics/facilities; and any other entity providing general and/or specialized healthcare regimen, assessment, maintenance, therapy, medication, and/or advice relating to all, or any portion of, a healthcare consumer's state of health, including but not limited to: general medical, specialized medical, surgical, dental, vision, psychological, and/or any other type of healthcare regimen, assessment, maintenance, therapy, medication, and/or advice.

Herein, the term "healthcare regimen" includes one or more medications and/or medication regimes; physical therapy; recommended dietary changes; lab work, recommended activity level changes; other lifestyle changes; and/or surgical procedures; and/or any prescribed and/or suggested regime, medication, treatment, activity, avoided activity, and/or program designed to improve, maintain, and/or slow the degradation of, a healthcare consumer's health and/or any general and/or specialized healthcare regimen, assessment, maintenance, therapy, medication, and/or advice relating to all, or any portion of, a healthcare consumer's state of health, including but not limited to: general medical, specialized medical, surgical, dental, vision, psychological, and/or any other type of healthcare regimen, assessment, maintenance, therapy, medication, and/or advice.

Herein, the terms "healthcare insurance plan", "healthcare benefit plan", "health insurance plan" and "health insurance program" are used interchangeably to denote any policy, program, means and/or mechanism whereby a healthcare consumer is provided healthcare benefits and/or healthcare services and/or entitlements to any form of healthcare.

In accordance with one embodiment, a method and system for image based nutrition monitoring includes a process for image based nutrition monitoring whereby, in one embodiment, data indicating a user's desired, and/or mandated/prescribed, dietary guidelines and/or restrictions is obtained from one or more sources. In one embodiment, when the user is frequenting a restaurant, fast food establishment, supermarket, or any other establishment for obtaining food, an optical image of printed or visual nutritional information associated with the food item the user is contemplating purchasing/eating is obtained via one or more user computing systems. In one embodiment, Optical Character Recognition (OCR) technology is used to transform the printed/visual nutritional information contained in the optical image into discrete nutritional information data. The nutritional information data is then analyzed and compared with the data indicating the user's desired, and/or mandated/prescribed, dietary guidelines and/or restrictions. In one embodiment, based, at least in part, on this analysis and comparison, and, in one embodiment, on data indicating the users recent nutritional/food intake, a recommendation is made to the user as to whether the contemplated food item is a good/acceptable purchase for the user, and/or whether the user should eat/purchase the food item. In one embodiment, the user is additionally provided with advice regarding limitations on future food purchases, and/or intake, which should be considered if the contemplated food item is indeed consumed.

Figure 2:
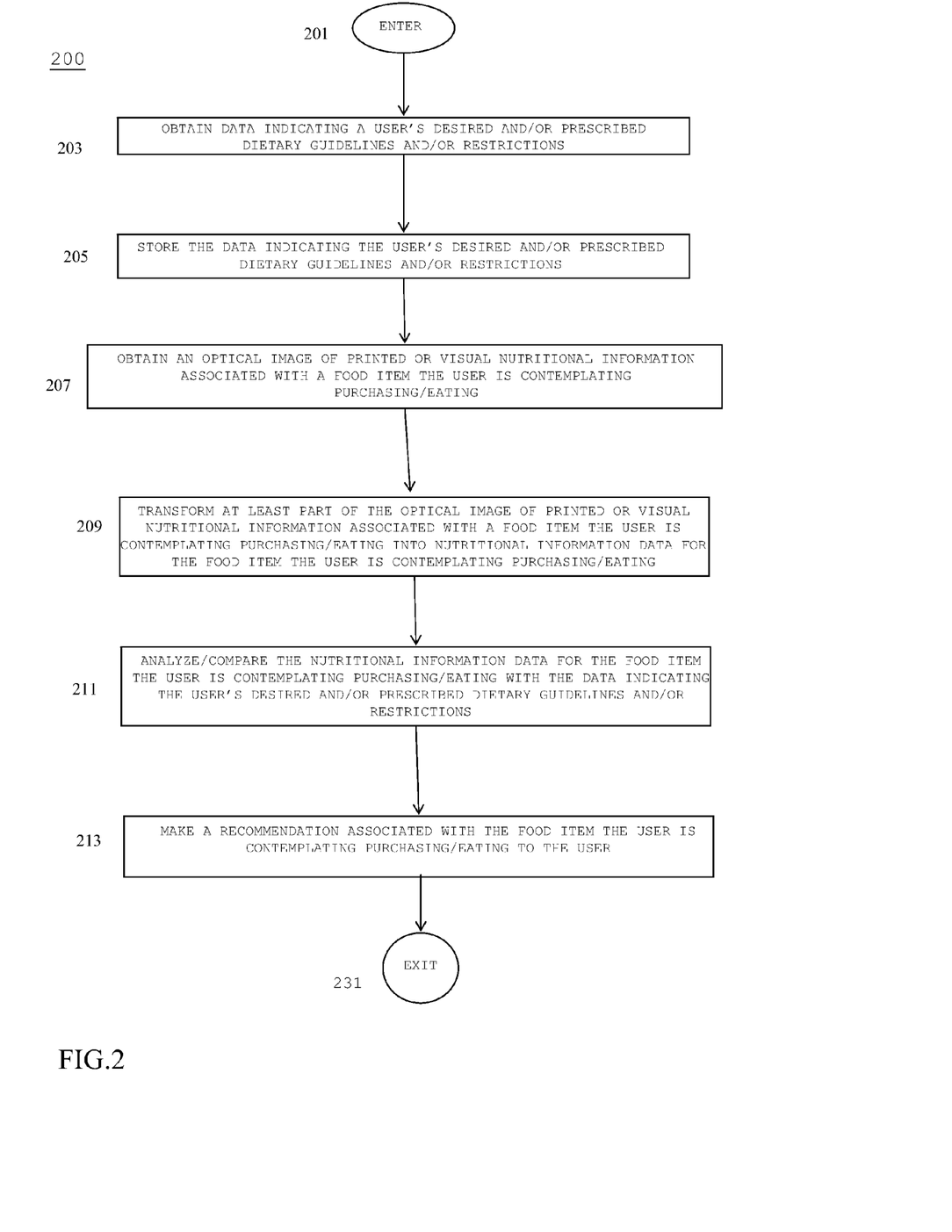
FIG. 2 is a flow chart depicting a process for image based nutrition monitoring in accordance with one embodiment.

FIG. 2 a flow chart depicting a process for image based nutrition monitoring 200 in accordance with one embodiment. In one embodiment, process for image based nutrition monitoring 200 is implemented, at least in part, and/or associated with, one or more user computing systems, such as user computing system 100 of FIG. 1, that include a camera, or other optical image capturing capability, such as a scanner, such as optical scan/camera capability 109 of FIG. 1.

Herein the term "computing system" includes, but is not limited to, any computing system known in the art at the time of filing, and/or as developed after the time of filing, such as, but not limited to: a mobile computing system; a desktop computing system; a laptop computing system; a notebook computing system; a workstation; a two-way pager; a cellular telephone; a smart phone; a digital wireless telephone; a Personal Digital Assistant (PDA); a server computer; an Internet appliance, and/or any other device, or any desired combination of these devices, that includes components that can execute all, or part, of a process for image based nutrition monitoring in accordance with at least one of the embodiments as discussed herein, and/or as known in the art at the time of filing, and/or as developed after the time of filing.

In one embodiment, the user computing system including a camera and/or optical image capture capability, such as user computing system 100 of FIG. 1, is a mobile computing system. Herein, the term "mobile computing system" includes, but not limited to: a mobile phone; a smart phone; an internet appliance; any SMS capable system; or any other mobile computing system as discussed herein, and/or as known in the art at the time of filing, and/or as developed after the time of filing.

Returning to FIG. 2, in one embodiment, process for image based nutrition monitoring 200 begins at ENTER OPERATION 201 of FIG. 2 and process flow proceeds to OBTAIN DATA INDICATING A USER'S DESIRED AND/OR PRESCRIBED DIETARY GUIDELINES AND/OR RESTRICTIONS OPERATION 203.

In one embodiment, at OBTAIN DATA INDICATING A USER'S DESIRED AND/OR PRESCRIBED DIETARY GUIDELINES AND/OR RESTRICTIONS OPERATION 203, data indicating a user's desired, and/or mandated/prescribed, dietary guidelines and/or restrictions is obtained from one or more sources.

In various embodiments, at OBTAIN DATA INDICATING A USER'S DESIRED AND/OR PRESCRIBED DIETARY GUIDELINES AND/OR RESTRICTIONS OPERATION 203 the user's desired, and/or mandated/prescribed, dietary guidelines/restrictions data is obtained from one or more sources including, but not limited to, the user's medical records as maintained by the user.

In various embodiments, at OBTAIN DATA INDICATING A USER'S DESIRED AND/OR PRESCRIBED DIETARY GUIDELINES AND/OR RESTRICTIONS OPERATION 203 the user's desired, and/or mandated/prescribed, dietary guidelines/restrictions data is obtained from one or more sources including, but not limited to, the user's medical records as maintained by, and/or associated with, one or more healthcare service providers associated with the user, such as the user's primary care physician, in one or more medical data websites/computing systems, such as medical data website/computing system 150 of FIG. 1, and/or database 170 of FIG. 1.

Returning to FIG. 2, in various embodiments, at OBTAIN DATA INDICATING A USER'S DESIRED AND/OR PRESCRIBED DIETARY GUIDELINES AND/OR RESTRICTIONS OPERATION 203 the user's desired, and/or mandated/prescribed, dietary guidelines/restrictions data is obtained from one or more sources including, but not limited to, one or more computing systems, data management systems, databases, and/or websites, such as website/computing system 150 of FIG. 1, and/or database 170 of FIG. 1, maintained by, and/or associated with, one or more data management systems, such as the QuickenHealth™ series of systems available from Intuit, Inc. of Mountain View, Calif.

Returning to FIG. 2, in various embodiments, at OBTAIN DATA INDICATING A USER'S DESIRED AND/OR PRESCRIBED DIETARY GUIDELINES AND/OR RESTRICTIONS OPERATION 203 the user's desired, and/or mandated/prescribed, dietary guidelines/restrictions data is obtained from one or more sources including, but not limited to, one or more computing systems, data management systems, databases, and/or websites, such as website/computing system 150 of FIG. 1, and/or database 170 of FIG. 1, maintained by, and/or associated with, one or more healthcare insurance providers associated with the user.

Returning to FIG. 2, in various embodiments, at OBTAIN DATA INDICATING A USER'S DESIRED AND/OR PRESCRIBED DIETARY GUIDELINES AND/OR RESTRICTIONS OPERATION 203 the user's desired, and/or mandated/prescribed, dietary guidelines/restrictions data is obtained from one or more sources including, but not limited to, one or more computing systems, data management systems, databases, and/or websites, such as website/computing system 150 of FIG. 1, and/or database 170 of FIG. 1, maintained by, and/or associated with, one or more health related agencies such as, but not limited to, the Food and Drug Administration (FDA), the American Heart Association (AHA), the American Cancer Society (ACS), the Mayo Clinic, etc.

Returning to FIG. 2, in various embodiments, at OBTAIN DATA INDICATING A USER'S DESIRED AND/OR PRESCRIBED DIETARY GUIDELINES AND/OR RESTRICTIONS OPERATION 203 the user's desired, and/or mandated/prescribed, dietary guidelines/restrictions data is obtained from one or more sources including, but not limited to, one or more computing systems, data management systems, databases, and/or websites, such as website/computing system 150 of FIG. 1, and/or database 170 of FIG. 1, maintained by, and/or associated with, one or more diet providers and/or diet plan developers/promoters.

Returning to FIG. 2, In various embodiments, the user's desired, and/or mandated/prescribed, dietary guidelines/restrictions data is obtained from one or more sources including, but not limited to, manual input provided by the user through a user computing system, such as user computing system 100 of FIG. 1, and one or more user interface devices such as, but not limited to, a keyboard, mouse, touch bad, touchscreen, voice recognition system, or any other device or mechanism for transforming one or more user actions into computer executable instructions and/or actions.

In various embodiments, the user's desired, and/or mandated/prescribed, dietary guidelines/restrictions data is obtained from any source of dietary guidelines/restrictions data as discussed herein, and/or as known/available in the art at the time of filing, and/or as known/developed after the time of filing.

In one embodiment, once data indicating a user's desired, and/or mandated/prescribed, dietary guidelines and/or restrictions is obtained from one or more sources at OBTAIN DATA INDICATING A USER'S DESIRED AND/OR PRESCRIBED DIETARY GUIDELINES AND/OR RESTRICTIONS OPERATION 203, process flow proceeds to STORE THE DATA INDICATING THE USER'S DESIRED AND/OR PRESCRIBED DIETARY GUIDELINES AND/OR RESTRICTIONS OPERATION 205.

In one embodiment, at STORE THE DATA INDICATING THE USER'S DESIRED AND/OR PRESCRIBED DIETARY GUIDELINES AND/OR RESTRICTIONS OPERATION 205 the user's desired, and/or mandated/prescribed, dietary guidelines/restrictions data of OBTAIN DATA INDICATING A USER'S DESIRED AND/OR PRESCRIBED DIETARY GUIDELINES AND/OR RESTRICTIONS OPERATION 203 is stored/saved in a database or any computing system, as discussed herein, and/or as known in the art/available at the time of filing, and/or as developed/made available after the time of filing.

In one embodiment, at STORE THE DATA INDICATING THE USER'S DESIRED AND/OR PRESCRIBED DIETARY GUIDELINES AND/OR RESTRICTIONS OPERATION 205 the user's desired, and/or mandated/prescribed, dietary guidelines/restrictions data of OBTAIN DATA INDICATING A USER'S DESIRED AND/OR PRESCRIBED DIETARY GUIDELINES AND/OR RESTRICTIONS OPERATION 203 is stored/saved in a database or any computing system, such as database 170 of FIG. 1, and/or any designated server system or computing system, such as systems 100, 150 or 120 of FIG. 1, or a designated portion of one or more server systems or computing systems, or a distributed database, or an external and/or portable hard drive.

For instance, in one embodiment, the user's desired, and/or mandated/prescribed, dietary guidelines/restrictions data is saved/stored in whole, or in part, in a memory system, such as memories 103, 153 and/or 123 of FIG. 1, or in a cache memory, or in any main memory or mass memory, associated with any computing system as discussed herein, and/or as known/available in the art at the time of filing, and/or as developed/made available after the time of filing.

In one embodiment, the user's desired, and/or mandated/prescribed, dietary guidelines/restrictions data in whole, or in part, is stored in any computing system and/or server system, or other device, in another location, or on/in a computer readable medium, and/or any other computer program product, as defined herein. In one embodiment, the user's desired, and/or mandated/prescribed, dietary guidelines/restrictions data in whole, or in part, is stored on a webpage, in a web-based system, or on a public network such as the Internet.

In some embodiments, the user's desired, and/or mandated/prescribed, dietary guidelines/restrictions data, stored as described above, is maintained, in whole, or in part, by: process for image based nutrition monitoring 200, and/or a provider of process for image based nutrition monitoring 200; a data management system, and/or a provider of a data management system; a healthcare service provider; a healthcare insurance provider; a third party data storage institution; any third party service or institution; and/or any other parties.

In some of these embodiments, access to the data is provided to process for image based nutrition monitoring 200 by providing access to the data and/or providing the data on a computer program product.

In one embodiment, once the user's desired, and/or mandated/prescribed, dietary guidelines/restrictions data of OBTAIN DATA INDICATING A USER'S DESIRED AND/OR PRESCRIBED DIETARY GUIDELINES AND/OR RESTRICTIONS OPERATION 203 is stored/saved at STORE THE DATA INDICATING THE USER'S DESIRED AND/OR PRESCRIBED DIETARY GUIDELINES AND/OR RESTRICTIONS OPERATION 205, process flow proceeds to OBTAIN AN OPTICAL IMAGE OF PRINTED OR VISUAL NUTRITIONAL INFORMATION ASSOCIATED WITH A FOOD ITEM THE USER IS CONTEMPLATING PURCHASING/EATING OPERATION 207.

In one embodiment, at OBTAIN AN OPTICAL IMAGE OF PRINTED OR VISUAL NUTRITIONAL INFORMATION ASSOCIATED WITH A FOOD ITEM THE USER IS CONTEMPLATING PURCHASING/EATING OPERATION 207, an optical image of printed or visual nutritional information associated with a food item the user is contemplating purchasing/eating is obtained via one or more user computing systems.

As noted above, recently restaurants, fast food establishments, supermarkets, and providers of food items have begun providing nutritional information regarding their food related offerings in printed formats, such as on menus, labels, flyers, and visual displays.

In one embodiment, at OBTAIN AN OPTICAL IMAGE OF PRINTED OR VISUAL NUTRITIONAL INFORMATION ASSOCIATED WITH A FOOD ITEM THE USER IS CONTEMPLATING PURCHASING/EATING OPERATION 207 when the user is frequenting a restaurant, fast food establishment, supermarket, or any other establishment for obtaining food, the user uses a user computing system, such as user computing system 100 of FIG. 1, and camera or other optical image capturing capability, such as optical scan/camera capability 109 of FIG. 1, to obtain an optical image, such as image data 111 of FIG. 1, of the printed or visual nutritional information associated with a food item the user is contemplating purchasing/eating.

Returning to FIG. 2, in one embodiment, once, an optical image of printed or visual nutritional information associated with a food item the user is contemplating purchasing/eating is obtained via one or more user computing systems at OBTAIN AN OPTICAL IMAGE OF PRINTED OR VISUAL NUTRITIONAL INFORMATION ASSOCIATED WITH A FOOD ITEM THE USER IS CONTEMPLATING PURCHASING/EATING OPERATION 207, process flow proceeds to TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209.

In one embodiment, at TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209 Optical Character Recognition (OCR) technology is used to transform at least a portion of the printed/visual nutritional information contained in the optical image of OBTAIN AN OPTICAL IMAGE OF PRINTED OR VISUAL NUTRITIONAL INFORMATION ASSOCIATED WITH A FOOD ITEM THE USER IS CONTEMPLATING PURCHASING/EATING OPERATION 207 into discrete nutritional information data.

In one embodiment, at TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209, at least a portion of the captured optical image of the printed or visual nutritional information, such as image data 111 of FIG. 1, is processed and transformed using OCR technology, such as OCR capability 104 of FIG. 1, under the control of one or more processors, such as processors 101, and/or 121, and/or 151, associated with one or more computing systems, such as user computing system 100, process computing system 120, and/or medical data website/computing system 150. In one embodiment, the OCR technology, such as OCR capability 104 of FIG. 1, is used by one or more processors such as processors 101, and/or 121, and/or 151, associated with one or more computing systems, such as user computing system 100, process computing system 120, and/or medical data website/computing system 150, to transform at least a portion the printed/visual nutritional information contained in the optical image, such as image data 111, into discrete nutritional information data, such as nutritional information data 106 of FIG. 1.

Returning to FIG. 2, once OCR technology is used to transform at least a portion of the printed/visual nutritional information contained in the optical image of OBTAIN AN OPTICAL IMAGE OF PRINTED OR VISUAL NUTRITIONAL INFORMATION ASSOCIATED WITH A FOOD ITEM THE USER IS CONTEMPLATING PURCHASING/EATING OPERATION 207 into discrete nutritional information data at TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209 process flow proceeds to ANALYZE/COMPARE THE NUTRITIONAL INFORMATION DATA FOR THE FOOD ITEM THE USER IS CONTEMPLATING PURCHASING/EATING WITH THE DATA INDICATING THE USER'S DESIRED AND/OR PRESCRIBED DIETARY GUIDELINES AND/OR RESTRICTIONS OPERATION 211.

In one embodiment, at ANALYZE/COMPARE THE NUTRITIONAL INFORMATION DATA FOR THE FOOD ITEM THE USER IS CONTEMPLATING PURCHASING/EATING WITH THE DATA INDICATING THE USER'S DESIRED AND/OR PRESCRIBED DIETARY GUIDELINES AND/OR RESTRICTIONS OPERATION 211 the nutritional information data of TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209 is analyzed and compared with the data indicating the user's desired, and/or mandated/prescribed, dietary guidelines and/or restrictions of STORE THE DATA INDICATING THE USER'S DESIRED AND/OR PRESCRIBED DIETARY GUIDELINES AND/OR RESTRICTIONS OPERATION 205.

In one embodiment, at ANALYZE/COMPARE THE NUTRITIONAL INFORMATION DATA FOR THE FOOD ITEM THE USER IS CONTEMPLATING PURCHASING/EATING WITH THE DATA INDICATING THE USER'S DESIRED AND/OR PRESCRIBED DIETARY GUIDELINES AND/OR RESTRICTIONS OPERATION 211 the nutritional information data of TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209 is analyzed and compared with the data indicating the user's desired, and/or mandated/prescribed, dietary guidelines and/or restrictions of STORE THE DATA INDICATING THE USER'S DESIRED AND/OR PRESCRIBED DIETARY GUIDELINES AND/OR RESTRICTIONS OPERATION 205 using one or more processors, such as processors 101, and/or 121, and/or 151, associated with one or more computing systems, such as user computing system 100, process computing system 120, and/or medical data website/computing system 150.

Returning to FIG. 2, as a specific illustrative example, in one embodiment at ANALYZE/COMPARE THE NUTRITIONAL INFORMATION DATA FOR THE FOOD ITEM THE USER IS CONTEMPLATING PURCHASING/EATING WITH THE DATA INDICATING THE USER'S DESIRED AND/OR PRESCRIBED DIETARY GUIDELINES AND/OR RESTRICTIONS OPERATION 211 the nutritional information data, such as nutritional information data 106 of FIG. 1, is analyzed using one or more processors associated with one or more computing systems such as processors 101, and/or 121, and/or 151, associated with one or more computing systems, such as user computing system 100, process computing system 120, and/or medical data website/computing system 150, to determine the sugar content, and/or carbohydrate content, of a given food item and then this data is compared with sugar and/or carbohydrate intake guidelines provided by a user's physician, such as nutritional requirements data 102, using one or more processors associated with one or more computing systems, such as processors 101, and/or 121, and/or 151, associated with one or more computing systems, such as user computing system 100, process computing system 120, and/or medical data website/computing system 150.

Returning to FIG. 2, in one embodiment, a history of the nutritional information data of TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209 associated with the user is saved/stored for at least a defined time frame and, in one embodiment, the nutritional information data associated with the food item currently being considered is combined with nutritional information data associated with food items recently purchased and or consumed by the user using one or more processors associated with one or more computing systems. In one embodiment, the combined data is then analyzed and compared with the data indicating the user's desired, and/or mandated prescribed, dietary guidelines and/or restrictions using one or more processors associated with one or more computing systems.

Returning to FIG. 2, as a specific illustrative example, in one embodiment at ANALYZE/COMPARE THE NUTRITIONAL INFORMATION DATA FOR THE FOOD ITEM THE USER IS CONTEMPLATING PURCHASING/EATING WITH THE DATA INDICATING THE USER'S DESIRED AND/OR PRESCRIBED DIETARY GUIDELINES AND/OR RESTRICTIONS OPERATION 211 in one embodiment the nutritional information data, such as nutritional information data 106 for a menu item, such as a specific dinner selection, is analyzed using one or more processors associated with one or more computing systems, such as processors 101, and/or 121, and/or 151, associated with one or more computing systems, such as user computing system 100, process computing system 120, and/or medical data website/computing system 150, to determine the calories of the specific dinner selection. Then this data is combined with additional nutritional information data, such as nutritional information data 106, and, in particular, the caloric information, associated with the other food selections made and entered into process for image based nutrition monitoring 200 by the user within the last 24 hours. Then the combined caloric intake for the past 24 hours is compared with FDA guidelines for the number of calories that should be consumed by a person similar to the user using one or more processors associated with one or more computing systems such as processors 101, and/or 121, and/or 151, associated with one or more computing systems, such as user computing system 100, process computing system 120, and/or medical data website/computing system 150.

In one embodiment, once the nutritional information data of TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209 is analyzed and compared with the data indicating the user's desired, and/or mandated/prescribed, dietary guidelines and/or restrictions of STORE THE DATA INDICATING THE USER'S DESIRED AND/OR PRESCRIBED DIETARY GUIDELINES AND/OR RESTRICTIONS OPERATION 205 at ANALYZE/COMPARE THE NUTRITIONAL INFORMATION DATA FOR THE FOOD ITEM THE USER IS CONTEMPLATING PURCHASING/EATING WITH THE DATA INDICATING THE USER'S DESIRED AND/OR PRESCRIBED DIETARY GUIDELINES AND/OR RESTRICTIONS OPERATION 211 process flow proceeds to MAKE A RECOMMENDATION ASSOCIATED WITH THE FOOD ITEM THE USER IS CONTEMPLATING PURCHASING/EATING TO THE USER OPERATION 213.

In one embodiment, at MAKE A RECOMMENDATION ASSOCIATED WITH THE FOOD ITEM THE USER IS CONTEMPLATING PURCHASING/EATING TO THE USER OPERATION 213 based, at least in part, on the analysis and comparison ANALYZE/COMPARE THE NUTRITIONAL INFORMATION DATA FOR THE FOOD ITEM THE USER IS CONTEMPLATING PURCHASING/EATING WITH THE DATA INDICATING THE USER'S DESIRED AND/OR PRESCRIBED DIETARY GUIDELINES AND/OR RESTRICTIONS OPERATION 211 a recommendation is made to the user as to whether the contemplated food item is a good/acceptable purchase for the user, and/or whether the user should eat/purchase the food item.

In one embodiment, at MAKE A RECOMMENDATION ASSOCIATED WITH THE FOOD ITEM THE USER IS CONTEMPLATING PURCHASING/EATING TO THE USER OPERATION 213 based, at least in part, on the analysis and comparison of the data indicating the user's desired, and/or mandated/prescribed, dietary guidelines and/or restrictions of OBTAIN DATA INDICATING A USER'S DESIRED AND/OR PRESCRIBED DIETARY GUIDELINES AND/OR RESTRICTIONS OPERATION 203 and the nutritional information data associated with the food item currently under consideration of TRANSFORM AT LEAST PART OF THE OPTICAL IMAGE OF PRINTED OR VISUAL NUTRITIONAL INFORMATION ASSOCIATED WITH A FOOD ITEM THE USER IS CONTEMPLATING PURCHASING/EATING INTO NUTRITIONAL INFORMATION DATA FOR THE FOOD ITEM THE USER IS CONTEMPLATING PURCHASING/EATING OPERATION 209, and, in one embodiment, data associated with food items recently consumed, performed at ANALYZE/COMPARE THE NUTRITIONAL INFORMATION DATA FOR THE FOOD ITEM THE USER IS CONTEMPLATING PURCHASING/EATING WITH THE DATA INDICATING THE USER'S DESIRED AND/OR PRESCRIBED DIETARY GUIDELINES AND/OR RESTRICTIONS OPERATION 211, recommendation data, such as recommendation data 108 of FIG. 1, is generated and made available to a computing system, such as user computing system 100 accessible by the user.

In various embodiments, the recommendation data, such as recommendation data 108 of FIG. 1, represents a recommendation to the user as to whether the contemplated food item is a good/acceptable purchase for the user, and/or whether the user should eat/purchase the food item.

Returning to FIG. 2, in one embodiment, at MAKE A RECOMMENDATION ASSOCIATED WITH THE FOOD ITEM THE USER IS CONTEMPLATING PURCHASING/EATING TO THE USER OPERATION 213 the user is additionally provided with advice regarding limitations on future food purchases, and/or intake, which should be considered if the contemplated food item is indeed consumed.

For instance, as one specific illustrative example, if the user decides to consume a food item whose nutritional information data indicated 2000 calories, and the FDA recommendation for total caloric intake for the user is 2500 calories per day, in one embodiment, at MAKE A RECOMMENDATION ASSOCIATED WITH THE FOOD ITEM THE USER IS CONTEMPLATING PURCHASING/EATING TO THE USER OPERATION 213, the process for image based nutrition monitoring would inform the user that the user can only consume 500 more calories that day and/or may recommend the user consider eating lightly the remainder of the day.

In one embodiment, once a recommendation is made to the user as to whether the contemplated food item is a good/acceptable purchase for the user, and/or whether the user should eat/purchase the food item at MAKE A RECOMMENDATION ASSOCIATED WITH THE FOOD ITEM THE USER IS CONTEMPLATING PURCHASING/EATING TO THE USER OPERATION 213, process flow proceeds to EXIT OPERATION 231.

In one embodiment, at EXIT OPERATION 231 process for image based nutrition monitoring 200 is exited to await new data.

Using process for image based nutrition monitoring 200, readily and commonly available image capture technology, such as a camera function on a mobile phone, and Optical Character Recognition (OCR) technology, is used to capture printed nutritional information regarding contemplated food purchases and transform the printed nutritional information into usable nutritional information data that can be analyzed by one or more processors associated with one or more computing systems. The nutritional information data so obtained is then processed and compared with data representing the individual nutritional desires/needs of the user by one or more processors so that the user can easily, efficiently, and semi-automatically, track their nutritional intake and obtain dietary advice that is consistent with the user's specific nutritional and/or dietary requirements, and/or dietary limitations.

As a result, process for image based nutrition monitoring 200 provides users the ability to easily and efficiently maintain healthy eating habits in virtually all circumstances, including in situations when the user dines out and/or is in the store contemplating a food purchase.

As discussed in more detail above, using the above embodiments, with little or no modification and/or healthcare consumer input, there is considerable flexibility, adaptability, and opportunity for customization to meet the specific needs of various healthcare consumers under numerous circumstances.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

As discussed in more detail above, using the above embodiments, with little or no modification and/or user input, there is considerable flexibility, adaptability, and opportunity for customization to meet the specific needs of various users under numerous circumstances.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, or protocols. Further, the system or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic or algorithm-like descriptions and representations are the means used by those of skill in the art to most effectively and efficiently convey the substance of their work to others of skill in the art. These operations, while described functionally or logically, are understood to be implemented by computer programs or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "activating", "accessing", "applying", "analyzing", "calculating", "capturing", "categorizing", "classifying", "comparing", "defining", "detecting", "determining", "distributing", "encrypting", "extracting", "filtering", "forwarding", "generating", "identifying", "implementing", "monitoring", "obtaining", "processing", "providing", "receiving", "requesting", "saving", "sending", "storing", "transferring", "transforming", "using", etc. refer to the action and process of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic or algorithmic-like form. It should be noted that the process steps or operations and instructions of the present invention can be embodied in software, firmware, or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as discussed herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s, or as discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A method for image based nutrition monitoring comprising:
    obtaining data indicating a user's desired or prescribed dietary guidelines or restrictions, at least a portion of the data being obtained from medical records data of the user, the medical records being maintained by a physician of the user;
    obtaining image data of printed nutritional information associated with a food item the user is considering;
    transforming at least a portion of the image data of the printed nutritional information associated with the food item the user is considering into nutritional information data associated with the food item the user is considering;
    analyzing or comparing the nutritional information data and the data indicating a user's desired or prescribed dietary guidelines or restrictions; and
    based, at least in part, on the analysis or comparison of the nutritional information data and the data indicating a user's desired or prescribed dietary guidelines or restrictions, make a consumption recommendation associated with the food item the user is considering to the user.

2. The method for image based nutrition monitoring of claim 1, wherein;
    at least a portion of the data indicating the user's desired or prescribed dietary guidelines or restrictions is obtained from one or more healthcare insurance providers.

3. The method for image based nutrition monitoring of claim 1, wherein;
    at least a portion of the data indicating the user's desired or prescribed dietary guidelines or restrictions is obtained from one or more health related/advisory agencies.

4. The method for image based nutrition monitoring of claim 1, wherein;
    at least a portion of the data indicating the user's desired or prescribed dietary guidelines or restrictions is obtained from one or more one or more diet providers or diet plan developers/promoters.

5. The method for image based nutrition monitoring of claim 1, wherein;
    the image data of printed nutritional information associated with a food item the user is considering is obtained using a user computing system having an optical scan capability.

6. The method for image based nutrition monitoring of claim 5, wherein;
    the user computing system is a mobile computing system.

7. The method for image based nutrition monitoring of claim 1, wherein;
the image data of printed nutritional information associated with a food item the user is considering is obtained using a user computing system having a camera capability.

8. The method for image based nutrition monitoring of claim 7, wherein;
the user computing system is a mobile computing system.

9. The method for image based nutrition monitoring of claim 1, wherein;
at least a portion of the image data of the printed nutritional information associated with the food item the user is considering is transformed into nutritional information data associated with the food item the user is considering using Optical Character Recognition (OCR) technology.

10. The method for image based nutrition monitoring of claim 1, wherein;
the consumption recommendation associated with the food item the user is considering is a recommendation regarding whether the food item the user is considering should or should not be consumed.

11. The method for image based nutrition monitoring of claim 1, wherein;
the consumption recommendation associated with the food item the user is considering is a recommendation regarding what actions, or non-actions, will be required by the user if the food item the user is considering is consumed in order for the user to comply with the user's desired or prescribed dietary guidelines or restrictions.

12. A computing system implemented process for image based nutrition monitoring comprising:
using one or more processors to obtain data indicating a user's desired or prescribed dietary guidelines or restrictions, at least a portion of the data being obtained from medical records data of the user, the medical records being maintained by a physician of the user;
using one or more processors associated with a user computing system to obtain image data of printed nutritional information associated with a food item the user is considering;
using one or more processors to transform at least a portion of the image data of the printed nutritional information associated with the food item the user is considering into nutritional information data associated with the food item the user is considering;
using one or more processors to analyze or compare the nutritional information data and the data indicating a user's desired or prescribed dietary guidelines or restrictions; and
based, at least in part, on the analysis or comparison of the nutritional information data and the data indicating a user's desired or prescribed dietary guidelines or restrictions, using one or more processors to make a consumption recommendation associated with the food item the user is considering to the user.

13. The computing system implemented process for image based nutrition monitoring of claim 12, wherein;
at least a portion of the data indicating the user's desired or prescribed dietary guidelines or restrictions is obtained from one or more healthcare insurance providers.

14. The computing system implemented process for image based nutrition monitoring of claim 12, wherein;
at least a portion of the data indicating the user's desired or prescribed dietary guidelines or restrictions is obtained from one or more health related/advisory agencies.

15. The computing system implemented process for image based nutrition monitoring of claim 12, wherein;
at least a portion of the data indicating the user's desired or prescribed dietary guidelines or restrictions is obtained from one or more one or more diet providers or diet plan developers/promoters.

16. The computing system implemented process for image based nutrition monitoring of claim 12, wherein;
the image data of printed nutritional information associated with a food item the user is considering is obtained using a user computing system having an optical scan capability.

17. The computing system implemented process for image based nutrition monitoring of claim 16, wherein;
the user computing system is a mobile computing system.

18. The computing system implemented process for image based nutrition monitoring of claim 12, wherein;
the image data of printed nutritional information associated with a food item the user is considering is obtained using a user computing system having a camera capability.

19. The computing system implemented process for image based nutrition monitoring of claim 18, wherein;
the user computing system is a mobile computing system.

20. The computing system implemented process for image based nutrition monitoring of claim 12, wherein;
at least a portion of the image data of the printed nutritional information associated with the food item the user is considering is transformed into nutritional information data associated with the food item the user is considering using Optical Character Recognition (OCR) technology.

21. The computing system implemented process for image based nutrition monitoring of claim 12, wherein;
the consumption recommendation associated with the food item the user is considering is a recommendation regarding whether the food item the user is considering should or should not be consumed.

22. The computing system implemented process for image based nutrition monitoring of claim 12, wherein;
the consumption recommendation associated with the food item the user is considering is a recommendation regarding what actions, or non-actions, will be required by the user if the food item the user is considering is consumed in order for the user to comply with the user's desired or prescribed dietary guidelines or restrictions.

23. A system for image based nutrition monitoring comprising:
a user computing system, the user computing system having an optical scan or camera capability;
one or more computing systems having an Optical Character Recognition (OCR) capability;
one or more databases or computing systems, at least one of the one or more databases or computing systems including data indicating a user's desired or prescribed dietary guidelines or restrictions;
printed nutritional information associated with a food item; and
one or more processors associated with one or more computing systems, the one or more processors associated with one or more computing systems implementing at least part of a process for image based nutrition monitoring, the process for image based nutrition monitoring including:
using the one or more processors to obtain the data indicating a user's desired or prescribed dietary guidelines or restrictions from the one or more databases or computing systems, at least a portion of the data being obtained from medical records data of the user, the medical records being maintained by a physician of the user;

using the optical scan or camera capability of the user computing system to obtain image data of the printed nutritional information associated with a food item the user is considering;

using the one or more computing systems having an Optical Character Recognition (OCR) capability to transform at least a portion of the image data of the printed nutritional information associated with the food item the user is considering into nutritional information data associated with the food item the user is considering using the Optical Character Recognition (OCR) capability;

using the one or more processors to analyze or compare the nutritional information data and the data indicating a user's desired or prescribed dietary guidelines or restrictions; and based, at least in part, on the analysis or comparison of the nutritional information data and the data indicating a user's desired or prescribed dietary guidelines or restrictions, using the one or more processors to make a consumption recommendation associated with the food item the user is considering to the user.

24. The system for image based nutrition monitoring of claim 23, wherein;

at least a portion of the one or more databases or computing systems including the data indicating the user's desired or prescribed dietary guidelines or restrictions are associated with one or more healthcare insurance providers.

25. The system for image based nutrition monitoring of claim 23, wherein;

the one or more databases or computing systems including at least a portion of the data indicating the user's desired or prescribed dietary guidelines or restrictions are associated with one or more health related/advisory agencies.

26. The system for image based nutrition monitoring of claim 23, wherein;

the one or more databases or computing systems including at least a portion of the data indicating the user's desired or prescribed dietary guidelines or restrictions are associated with one or more one or more diet providers or diet plan developers/promoters.

27. The system for image based nutrition monitoring of claim 23, wherein;

the user computing system is a mobile computing system.

28. The system for image based nutrition monitoring of claim 23, wherein;

the consumption recommendation associated with the food item the user is considering is a recommendation regarding whether the food item the user is considering should or should not be consumed.

29. The system for image based nutrition monitoring of claim 23, wherein;

the consumption recommendation associated with the food item the user is considering is a recommendation regarding what actions, or non-actions, will be required by the user if the food item the user is considering is consumed in order for the user to comply with the user's desired or prescribed dietary guidelines or restrictions.

* * * * *

UNITED STATES PATENT AND TRADEMARK OFFICE
CERTIFICATE OF CORRECTION

Page 1 of 1

PATENT NO. : 8,630,448 B1
APPLICATION NO. : 13/274120
DATED : January 14, 2014
INVENTOR(S) : Elangovan Shanmugam et al.

It is certified that error appears in the above-identified patent and that said Letters Patent is hereby corrected as shown below:

In the Claims:

In Column 22, Line 57, Claim 4, after "from" delete "one or more";
In Column 24, Line 5, Claim 15, after "from" delete "one or more"; and
In Column 26, Line 11, Claim 26, after "with" delete "one or more".

Signed and Sealed this
Fifteenth Day of July, 2014

Michelle K. Lee
*Deputy Director of the United States Patent and Trademark Office*